United States Patent [19]

Bugner et al.

[11] Patent Number: 4,851,561
[45] Date of Patent: * Jul. 25, 1989

[54] QUATERNARY AMMONIUM SALTS

[75] Inventors: Douglas E. Bugner; Peter S. Alexandrovich, both of Rochester, N.Y.

[73] Assignee: Eastman Kodak Company, Rochester, N.Y.

[*] Notice: The portion of the term of this patent subsequent to Dec. 6, 2005 has been disclaimed.

[21] Appl. No.: 134,336

[22] Filed: Dec. 17, 1987

[51] Int. Cl.$^4$ .......................................... C07C 143/38
[52] U.S. Cl. ...................................................... 560/14
[58] Field of Search ........................................... 560/14

[56] References Cited

U.S. PATENT DOCUMENTS

| | | | |
|---|---|---|---|
| 3,893,935 | 7/1975 | Jadwin et al. | 252/62.1 |
| 4,139,483 | 2/1979 | Williams et al. | 252/62 |
| 4,323,634 | 4/1982 | Jadwin | 430/110 |
| 4,338,390 | 7/1982 | Lu | 430/106 |
| 4,394,430 | 7/1983 | Jadwin et al. | 430/110 |
| 4,490,455 | 12/1984 | Hoffend et al. | 430/110 |
| 4,684,596 | 8/1987 | Bonser et al. | 430/110 |

OTHER PUBLICATIONS

Chemical Abstracts Registration No. 65796-86-3.

Primary Examiner—Michael L. Shippen
Attorney, Agent, or Firm—David F. Janci

[57] ABSTRACT

New quaternary ammonium salts are provided having advantageous utility as charge agents in electrostatographic toners and developers. The salts have the structure

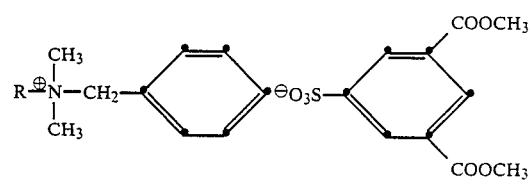

wherein R is alkyl having 12 to 18 carbon atoms.

2 Claims, No Drawings

4,851,561

QUATERNARY AMMONIUM SALTS

FIELD OF THE INVENTION

This invention relates to certain new quaternary ammonium salt chemical compounds which are useful as charge-control agents in dry electrostatographic toners and developers. More particularly, the new salts are thermally stable compounds that can be well-dispersed in typical toner binder materials to form toners having good charging properties without unacceptable interactions with other developer or copier components.

BACKGROUND

In electrostatography an image comprising an electrostatic field pattern, usually of non-uniform strength, (also referred to as an electrostatic latent image) is formed on an insulative surface of an electrostatographic element by any of various methods. For example, the electrostatic latent image may be formed electrophotographically (i.e., by imagewise photo-induced dissipation of the strength of portions of an electrostatic field of uniform strength previously formed on a surface of an electrophotographic element comprising a photoconductive layer and an electrically conductive substrate), or it may be formed by dielectric recording (i.e., by direct electrical formation of an electrostatic field pattern on a surface of a dielectric material). Typically, the electrostatic latent image is then developed into a toner image by contacting the latent image with an electrostatographic developer. If desired, the latent image can be transferred to another surface before development.

One well-known type of electrostatographic developer comprises a dry mixture of toner particles and carrier particles. Developers of this type are commonly employed in well-known electrostatographic development processes such as cascade development and magnetic brush development. The particles in such developers are formulated such that the toner particles and carrier particles occupy different positions in the triboelectric continuum, so that when they contact each other during mixing to form the developer, they become triboelectrically charged, with the toner particles acquiring a charge of one polarity and the carrier particles acquiring a charge of the opposite polarity. These opposite charges attract each other such that the toner particles cling to the surfaces of the carrier particles. When the developer is brought into contact with the latent electrostatic image, the electrostatic forces of the latent image (sometimes in combination with an additional applied field) attract the toner particles, and the toner particles are pulled away from the carrier particles and become electrostatically attached imagewise to the latent image-bearing surface. The resultant toner image can then be fixed in place on the surface by application of heat or other known methods (depending upon the nature of the surface and of the toner image) or can be transferred to another surface, to which it then can be similarly fixed.

A number of requirements are implicit in such development schemes. Namely, the electrostatic attraction between the toner and carrier particles must be strong enough to keep the toner particles held to the surfaces of the carrier particles while the developer is being transported to and brought into contact with the latent image, but when that contact occurs, the electrostatic attraction between the toner particles and the latent image must be even stronger, so that the toner particles are thereby pulled away from the carrier particles and deposited on the latent image-bearing surface. In order to meet these requirements for proper development, the level of electrostatic charge on the toner particles should be maintained within an adequate range.

The toner particles in dry developers often contain material referred to as a charge agent or charge-control agent, which helps to establish and maintain toner charge within an acceptable range. Many types of charge-control agents have been used and are described in the published patent literature.

One general type of known charge-control agent comprises a quaternary ammonium salt. While many such salts are known, some do not perform an adequate charge-control function in any type of developer, some perform the function well in only certain kinds of developers, and some control charge well but produce adverse side effects.

A number of quaternary ammonium salt charge-control agents are described, for example, in U.S. Pat. Nos. 4,684,596; 4,394,430; 4,338,390; 4,490,455; and 4,139,483. Unfortunately, many of those known charge-control agents exhibit one or more drawbacks in some developers.

For example, some of the known quaternary ammonium salt charge agents lack thermal stability and, thus, totally or partially decompose during attempts to mix them with known toner binder materials in well-known processes of preparing toners by mixing addenda with molten toner binders. Such processes are often referred to as melt-blending or melt-compounding processes and are commonly carried out at temperatures ranging from about 120° to about 200° C. Thus, charge agents that are thermally unstable at temperatures at or below 200° C. can exhibit this decomposition problem.

Also, some of the known quaternary ammonium salt charge-control agents have relatively high melting points. During melt-blending, a molten charge agent can be more quickly, efficiently, and uniformly dispersed in the molten toner binder than can a solid charge agent. Non-uniform dispersion can result in poor or inconsistent charge-control performance from toner particle to toner particle (among other undesirable effects discussed below). Therefore, it is a drawback to have a charge agent with a melting point higher than 120° C., because such a charge agent will be slowly, inefficiently, and non-uniformly dispersed in the toner binder during some melt-blending processes.

Furthermore, some of the known quaternary ammonium salt charge agents have relatively high electrical conductivity, which can lead to poor performance of some developers.

Also, some known quaternary ammonium salt charge agents exhibit high sensitivity to changes in environmental relative humidity and/or temperature, which can lead to erratic performance of the charge agents under changing environmental conditions.

Additionally, some of the known quaternary ammonium salt charge agents will adversely interact chemically and/or physically with other developer or copier components. For example, some will interact with carrier or carrier coating materials (e.g., fluorohydrocarbon polymer coatings such as poly(vinylidene fluoride)) and lead to premature carrier aging and shortened useful developer life. Some will interact with certain toner colorants to cause unacceptable hue shifts in the toner.

Some will interact with copier fuser rollers (e.g., rollers coated with fluorohydrocarbon polymers such as poly(vinylidene fluoride-co-hexafluoropropylene)) to cause premature failure of the copier's toner fusing system.

Also, poor dispersibility of some of the known quaternary ammonium salt charge agents in some of the known toner binder materials, either because the charge agent has a high melting point (as discussed above) or because it is incompatible with or otherwise poorly dispersible in the binder, can lead to worsening of some of the problems mentioned above. Non-uniform dispersion of charge agent means that higher concentrations or agglomerations of charge agent will exist in some portions of the toner binder mix, compared to others. In typical melt-blending processes, the toner mixture is cooled and ground down to desired particle size after melt-blending. Agglomerations of charge agent provide sites in the mixture where fracture is more likely to occur during grinding. The new surfaces created by such fracture will have a higher concentration of charge agent that will internal sites. Thus, the final toner particles will have a higher surface concentration of charge agent than internal concentration. It should be readily appreciated that if a charge agent tends to adversely interact with the environment, copier components, or other developer components, higher surface concentrations of charge agent on the toner particles will lead to a greater degree of such interaction, thus exacerbating problems such as high conductivity, high environmental sensitivity, and premature failure of carrier and fuser roll materials.

It would, therefore, be desirable to provide new quaternary ammonium salts that could perform the charge-controlling function well in dry electrographic toners and developers, while avoiding or minimizing all of the drawbacks noted above. The present invention does this.

SUMMARY OF THE INVENTION

The invention provides new quaternary ammonium salts having the structure

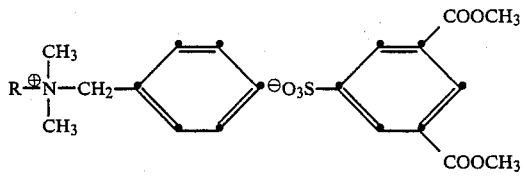

wherein R is alkyl having 12 to 18 carbon atoms.

The salts of the invention have advantageous utility as charge agents in dry, particulate, electrostatographic toners and developers. Such toners comprise a polymeric binder and a charge-control agent chosen from the inventive salts defined above. Such developers comprise carrier particles and the particulate toner defined above.

The new salts of the invention provide good charge-control in toners and developers. The inventive salts do not exhibit unacceptably high conductivity or environmental sensitivity. The salts have decomposition points well above 200° C. and melting points well below 120° C. and are quickly, efficiently and uniformly dispersed and structurally intact in toners prepared by melt-blending the salts with appropriate polymeric binders. The inventive salts have not been found to interact unacceptably with commonly utilized toner colorants, carrier materials, or copier components such as fuser rolls.

It should be noted that other new quaternary ammonium salts, different from the salts of the present invention, but devised to serve similar purposes, are described in copending U.S. patent application Ser. Nos. 134,409; 134,347; 134,479; 134,427, now U.S. Pat. No. 4,806,283; and 134,388, now U.S. Pat. No. 4,803,017, all filed Dec. 17, 1987. Also, inventive toners and developers containing charge agents comprising the salts of this invention or the other new salts, are described in copending U.S. patent application Ser. Nos. 134,285, now U.S. Pat. 4,812,381; 134,344; 134,478; now U.S. Pat. No. 4,812,378; 134,400, now U.S. Pat. No. 4,789,614; 134,411, now U.S. Pat. No. 4,812,382; and 134,399, now U.S. Pat. No. 4,812,380 filed Dec. 17, 1987. Among those applications, the one that claims toners and developers containing charge agents comprising the salts of the present invention is Application No. 134,400, now U.S. Pat. 4,789,614.

DESCRIPTION OF PREFERRED EMBODIMENTS

The new quaternary ammonium salts of the invention can be conveniently prepared from readily available starting materials, such as a halide salt of the appropriate benzyldimethyl(C12-18)alkylammonium monohydrate and an alkali metal salt of 3,5-dimethoxycarbonylbenzenesulfonate. For example, benzyldimethyloctadecylammonium chloride monohydrate is commercially available from Onyx Chemical Co., USA, under the trademark Ammonyx-4002, and sodium 3,5-dimethoxycarbonylbenzenesulfonate is commercially available from the Aldrich Chemical Company, USA. Aqueous solutions of these materials, in proportions to give a slight stoichiometric excess of the alkali metal salt of 3,5-dimethoxycarbonylbenzenesulfonate, are mixed together and spontaneously react to yield a precipitate of the desired new quaternary ammonium salt.

to be utilized as a charge-control agent in electrostatographic toners, the inventive quaternary ammonium salt is mixed in any convenient manner (preferably by melt-blending as described, for example, in U.S. Pat. Nos. 4,684,596 and 4,394,430) with an appropriate polymeric toner binder material and any other desired addenda, and the mix is then ground to desired size to form a free-flowing powder of toner particles containing the charge agent.

Such toner particles can have an average diameter between about 0.1 μm and about 100 μm, a value in the range from about 1.0 to about 30 μm being preferable for many currently used machines. However, larger or smaller particles may be needed for particular methods of development or development conditions.

Generally, it has been found desirable to add from about 0.05 to about 6 parts and preferably 0.05 to about 2.0 parts by weight of the aforementioned quaternary ammonium salts per 100 parts by weight of a polymer to obtain an improved toner composition. Although larger or smaller amounts of a charge control agent can be added, it has been found that if amounts much lower than those specified above are utilized, the charge-control agent tends to exhibit little or substantially no improvement in the properties of the toner composition. As amounts more than about 5 parts of charge-control agent per 100 parts of polymeric binder are added, it has been found that the net toner charge exhibited by the resultant toner composition tends to be reduced. Of course, it must be recognized that the optimum amount of charge-control agent to be added will depend, in part, on the particular quaternary ammonium charge-control agent selected and the particular polymer to which it is added. However, the amounts specified hereinabove are typical of the useful range of charge-control agent utilized in conventional dry toner materials.

The polymers useful as toner binders with the salts of the present invention can be used alone or in combination and include those polymers conventionally employed in electrostatic toners. Useful polymers generally have a glass transition temperature within the range of from 50° to 120° C. Preferably, toner particles prepared from these polymers have relatively high caking temperature, for example, higher than about 60° C., so that the toner powders can be stored for relatively long periods of time at fairly high temperatures without having individual particles agglomerate and clump together. The melting point of useful polymers preferably is within the range of from about 65° C. to about 200° C. so that the toner particles can readily be fused to a conventional paper receiving sheet to form a permanent image. Especially preferred polymers are those having a melting point within the range of from about 65° to about 120° C. Of course, where other types of receiving elements are used, for example, metal plates such as certain printing plates, polymers having a melting point and glass transition temperature higher than the values specified above can be used.

Among the various polymers which can be employed in toner particles with the salts of the present invention are polycarbonates, resin-modified maleic alkyd polymers, polyamides, phenol-formaldehyde polymers and various derivatives thereof, polyester condensates, modified alkyd polymers, aromatic polymers containing alternating methylene and aromatic units such as described in U.S. Pat. No. 3,809,554 and fusible cross-linked polymers as described in U.S. Pat. Re. No. 31,072.

Typical useful toner polymers include certain polycarbonates such as those described in U.S. Pat. No. 3,694,359, which include polycarbonate materials containing an alkylidene diarylene moiety in a recurring unit and having from 1 to about 10 carbon atoms in the alkyl moiety. Other useful polymers having the above-described physical properties include polymeric esters of acrylic and methacrylic acid such as poly(alkyl acrylate), and poly(alkyl methacrylate) wherein the alkyl moiety can contain from to about 10 carbon atoms. Additionally, other polyesters having the aforementioned physical properties are also useful. Among such other useful polyesters are copolyesters prepared from terephthalic acid (including substituted terephthalic acid), a bis(hydroxyalkoxy)phenylalkane having from 1 to 4 carbon atoms in the alkoxy radical and from 1 to 10 carbon atoms in the alkane moiety (which can also be a halogen-substituted alkane), and an alkylene glycol having from 1 to 4 carbon atoms in the alkylene moiety.

Other useful polymers are various styrene-containing polymers. Such polymers can comprise, e.g., a polymerized blend of from about 50 to about 100 percent by weight of styrene, from 0 to about 45 percent by weight of a lower alkyl acrylate or methacrylate having from 1 to about 4 carbon atoms in the alkyl moiety such as methyl, ethyl, isopropyl, butyl, etc. and from about 5 to about 40 percent by weight of another vinyl monomer other than styrene, for example, a higher alkyl acrylate or methacrylate having from about 6 to 20 or more carbon atoms in the alkyl group. Typical styrene-containing polymers prepared from a copolymerized blend as described hereinabove are copolymers prepared from a monomeric blend of 40 to 60 percent by weight styrene or styrene homolog, from about 20 to about 50 percent by weight of a lower alkyl acrylate or methacrylate and from about 5 to about 30 percent by weight of a higher alkyl acrylate or methacrylate such as ethylhexyl acrylate (e.g., styrene-butyl acrylate-ethylhexyl acrylate copolymer). Preferred fusible styrene copolymers are those which are covalently crosslinked with a small amount of a divinyl compound such as divinylbenzene. A variety of other useful styrenecontaining toner materials are disclosed in U.S. Pat. Nos. 2,918,460; Re. 25,316; 2,788,288; 2,638,416; 2,618,552 and 2,659,670.

Various kinds of well-known addenda (e.g., colorants, release agents, etc.) can also be incorporated into toners containing salts of the invention.

Numerous colorant materials selected from dyestuffs or pigments can be employed in such toners. Such materials serve to color the toner and/or render it more visible. Of course, suitable toner materials having the appropriate charging characteristics can be prepared without the use of a colorant material where it is desired to have developed image of low optical density. In those instances where it is desired to utilize a colorant, the colorants can, in principle, be selected from virtually any of the compounds mentioned in the Colour Index Volumes 1 and 2, Second Edition.

Included among the vast number of useful colorants are such materials as Hansa yellow G (C.I. 11680), Nigrosine Spirit soluble (C.I. 50415), Chromogen Black ETOO (C.I. 45170), Solvent Black 3 (C.I. 26150), Fuchsine N (C.I. 42510), C.I. Basic Blue 9 (C.I. 52015). Carbon black also provides a useful colorant. The amount of colorant added may vary over a wide range, for example, from about 1 to about 20 percent of the weight of the polymer. Particularly good results are obtained when the amount is from about 1 to about 10 percent.

To be utilized as toners in electrostatographic developers, toners containing salts of this invention can be mixed with a carrier vehicle. The carrier vehicles which can be used to form such developer compositions can be selected from a variety of materials. Such materials include carrier core particles and core particles overcoated with a thin layer of film-forming resin.

The carrier core materials can comprise conductive, non-conductive, magnetic, or non-magnetic materials. For example, carrier cores can comprise glass beads; crystals of inorganic salts such as aluminum potassium chloride; other salts such as ammonium chloride or sodium nitrate; granular zircon; granular silicon; silicon dioxide; hard resin particles such as poly(methyl methacrylate); metallic materials such as iron, steel, nickel, carborundum, cobalt, oxidized iron; or mixture or alloys of any of the foregoing. See, for example, U.S. Pat. Nos. 3,850,663 and 3,970,571. Especially useful in magnetic brush development schemes are iron particles such as porous iron particles having oxidized surfaces, steel particles, and other "hard" or "soft" ferromagnetic materials such as gamma ferric oxides or ferrites, such as ferrites of barium, strontium, lead, magnetism, or aluminum. See, for example, U.S. Pat. Nos. 4,052,518; 4,478,925; and 4,546,060.

As noted above, the carrier particles can be overcoated with a thin layer of a film-forming resin for the purpose of establishing the correct triboelectric relationship and charge level with the toner employed. Examples of suitable resins are the polymers described in U.S. Pat. Nos. 3,547,822; 3,632,512; 3,795,618 and 3,898,170 and Belgian Pat. No. 797,132. Other useful resins are fluorocarbons such as polytetrafluoroethylene, poly(vinylidene fluoride), mixtures of these, and copolymers of vinylidene fluoride and tetrafluoroethylene. See, for example, U.S. Pat. Nos. 4,545,060; 4,478,925; 4,076,857; and 3,970,571. Such polymeric fluorohydrocarbon carrier coatings can serve a number of known purpose. One such purposes can be to aid the developer to meet the electrostatic force requirements mentioned above by shifting the carrier particles to a position in the triboelectric series different from that of the uncoated carrier core material, in order to adjust the degree of triboelectric charging of both the carrier and toner particles. Another purpose can be to reduce the frictional characteristics of the carrier particles in order to improve developer flow properties. Still another purpose can be to reduce the surface hardness of the carrier particles so that they are less likely to break apart during use and less likely to abrade surfaces (e.g., photoconductive element surfaces) that they contact during use. Yet another purpose can be to reduce the tendency of toner material or other developer additives to become undesirable permanently adhered to carrier surfaces during developer use (often referred to as scumming). A further purpose can be to alter the electrical resistance of the carrier particles.

A typical developer composition containing the above-described toner and a carrier vehicle generally comprises from about 1 to about 20 percent by weight of particulate toner particles and from about 80 to about 99 percent by weight carrier particles. Usually, the carrier particles are larger than the toner particles. Conventional carrier particles have a parti cle size on the order of from about 20 to about 1200 microns, preferably 30–300 microns.

Alternatively, toners containing salts of the present invention can be used in a single component developer, i.e., with no carrier particles.

Toner and developer compositions containing salts of this invention can be used in a variety of ways to develop electrostatic charge patterns or latent images. Such developable charge patterns can be prepared by a number of means and be carried for example, on a light sensitive photoconductive element or a non-light-sensitive dielectric-surfaces element such as an insulator-coated conductive sheet. One suitable development technique involves cascading the developer composition across the electrostatic charge pattern, while another technique involves applying toner particles from a magnetic brush. This latter technique involves the use of a magnetically attractable carrier vehicle in forming the developer composition. After imagewise deposition of the toner particles, the image can be fixed, e.g., by heating the toner to cause it to fuse to the substrate carrying the toner. If desired, the unfused image can be transferred to a receiver such as a blank sheet of copy paper and then fused to form a permanent image.

The following examples are presented to further illustrate some preferred embodiments of the salts of the invention and to compare their properties and performance to those of salts outside the scope of the invention.

EXAMPLE 1—PREPARATION OF BENZYLDIMETHYLOCTADECYLAMMONIUM 3,5-DIMETHOXYCARBONYLBENZENESULFONATE

Benzyldimethyloctadecylammonium chloride monohydrate from Onyx Chemical Co. (68.2 g, 0.154 mole) was dissolved in hot water (1.5 l), and a solution of sodium 3,5-dimethoxycarbonylbenzenesulfonate from Aldrich Chemical Co. (50.2 g, 0.169 mole) in warm water (1.5 l) was added. A gummy precipitate formed, which was extracted with dichloromethane, dried, and treated with anhydrous diethyl ether to crystallize as fine white needles, which were collected by filtration, washed with additional ether, and dried in a vacuum oven (70° C.). The product, benzyldimethyloctadecylammonium 3,5-dimethoxycarbonylbenzenesulfonate, was characterized by a combination of nuclear magnetic resonance spectroscopy, infrared spectroscopy, combustion analysis, melting point, and thermogravimetric analysis.

Yield: 94.7 g (0.143 mole, 93.0%); mp: 79.5°–81.5° C.; $^1$H NMR (CDCl$_3$): δ 0.87 (t, 3H), 1.25 (m 3OH), 1.79 (m, 2H), 3.22 (s, 6H), 3,42 (m, 2H), 3.91 (s, 6H), 4,82 (s, 2H), 7.4–7.7 (m, 5H), 8.68 (s, 1H), and 8.80 ppm (s, 2H); IR (KBR): ν 1738, 1725, 1233, 1223, 760, 634, and 623 cm$^{-1}$; TGA (10° C./min, air: stable to 233° C. Atomic analysis calculated for C$_{37}$H$_{59}$NO$_7$S (661.94): 2.1% N, 67.1% C, 9.0% H, and 4.8% S. Found: 2.0% N, 67.4% C, 8.9% H, and 4.8% S.

The other salts within the scope of the invention are prepared similarly, with similar yields.

EXAMPLE 2—SALT MELTING POINT AND DECOMPOSITION POINT

The quaternary ammonium salt of Example 1 was compared to similar salts outside the scope of the present invention, in regard to melting point and decomposition point. Decomposition temperatures were measured in a DuPont Thermal Gravimetric Analyzer 1090. Results are presented in Table I.

TABLE I

| Salt | Of the Invention? | Melting Point(°C.) | Decomposition Point (°C.) |
|---|---|---|---|
| benzyldimethyloctadecylammonium 3,5-dimethoxycarbonylbenzene sulfonate | yes | 80–82 | 233 |
| benzyldimethyloctadecylammonium chloride | no | 145–146 | 160 |
| p-nitrobenzyldimethyloctadecylammonium chloride | no | 189–190 | 189 |
| benzyldimethyloctadecylammonium benzenesulfonate | no | 154–155 | 287 |
| benzyldimethyloctadecylammonium p-chlorobenzenesulfonate | no | 173–174 | 272 |
| benzyldimethyloctadecylammonium p-toluenesulfonate | no | 172–174 | 218 |

The data in Table I show that the inventive salt has a decomposition point well above 200° C. and a melting point well below 120° C., whereas the non-inventive salts have a decomposition point below 200° C. (indicating likely decomposition during some toner melt-blending processes) and/or a melting point above 120° C. (indicating likely slow, inefficient, and non-uniform dispersion in toner binder during some toner melt-blending processes).

EXAMPLE 3—CARRIER COATING INTERACTION TEST

A salt of the invention and non-inventive salts were tested for possible adverse interaction with a typical carrier material. Carrier samples were prepared as in U.S. Pat. No. 4,546,060, comprising strontium ferrite core material coated with a thin film of poly(vinylidene fluoride). The salts to be tested were coated from a dichloromethane solution onto the polymer-coated carrier samples to give a concentration of 4% salt and 96% polymer-coated carrier. A control for comparison purposes contained no salt on the polymer-coated carrier. All samples were exercised for 24 hours by placing them in vials on top of a typical, normally rotating, magnetic brush development apparatus. The salts were then extracted from the coated carriers with dichloromethane, and the carriers were dried. The charging capabilities of the carriers after this treatment were determined by mixing the carriers with a standard particulate toner and measuring the toner charge generated thereby in microcoulombs per gram ($\mu c/g$). In cases where no salt or a completely non-interactive salt were used, one would expect no change in charging capability after the treatment. Results are presented in Table II.

TABLE II

| Salt | Useful in Toners Of the Invention? | Charge after treatment ($\mu c/g$) | % decrease in charge because of treatment |
|---|---|---|---|
| none (control) | no | 29.7 | 0 (control) |
| benzyldimethyloctadecylammonium 3,5-dimethoxy-carbonylbenzenesulfonate | yes | 26.0 | 12.5 |
| benzyldimethyloctadecylammonium 2,4-dimethylbenzenesulfonate | no | 15.8 | 46.8 |
| benzyldimethyloctadecylammonium 2,5-dimethylbenzenesulfonate | no | 8.1 | 72.7 |
| benzyldimethyloctadecylammonium p-chlorobenzenesulfonate | no | 17.4 | 41.4 |
| benzyldimethyloctadecylammonium p-toluenesulfonate | no | 17.5 | 41.1 |
| benzyldimethyloctadecylammonium 2,4,5-trichlorobenzenesulfonate | no | 13.6 | 54.2 |
| phenethyldimethyloctadecylammonium p-toluenesulfonate | no | 14.1 | 52.5 |

The data in Table II indicate that the inventive salt interacted minimally with the coated carrier, producing a minimal decrease in charging capability; while the non-inventive salts decreased the charging capability of the carrier by much larger percentages, indicative of significant adverse interaction with the coated carrier.

EXAMPLE 4—FUSER ROLL COVER INTERACTION TEST

A salt of the invention and various salts outside the scope of the invention were tested for possible adverse interaction with a typical fuser roll cover material. Plaques of poly(vinylidene fluoride-co-hexafluoropropylene)containing some carbon filler were compression molded to about 1.9 mm thickness to represent typical fuser roll covers. The salts to be tested were placed on the plaques in 100 mg portions (dry, no solvent). A control plaque had nothing placed on it. The plaques were baked at about 190° C. for 24 hours in air to simulate heat fusing conditions and were allowed to cool to room temperature. The salts or their residues were removed from the plaques by rinsing with dichloromethane. Any visible cracks in the plaques were noted. Areas of the plaques contacted by the salts were subjected to thermogravimetric analysis to determine their decomposition points. Results are presented in Table III.

TABLE III

| Salt | Of the Invention? | Observed Cracking? | Decomposition point of treated cover (°C.) |
|---|---|---|---|
| none (control) | no | no | 404.2 |
| benzyldimethyloctadecylammonium 3,5-dimethoxycarbonylbenzenesulfonate | yes | no | 383.4 |
| benzyldimethyloctadecylammonium p-toluenesulfonate | no | no | 377.3 |
| phenethyldimethyloctadecylammonium p-toluenesulfonate | no | no | 329.3 |
| benzyldimethyloctadecylammonium chloride | no | yes | 400.8 |

The data in Table III indicate that contact with an inventive salt under heat fusing conditions produced minimal effect on the fuser cover material, while contact with salts outside the scope of the invention either produced cracks in the cover material or lowered its thermal stability more significantly. The lack of adverse lowering of decomposition point in the sample contacted with benzyldimethyloctadecylammonium chloride (although cracking did occur) may be because significant decomposition of that non-inventive salt occurs at temperatures well below that used in the test. (See Table I)

EXAMPLE 5—TONERS AND DEVELOPERS

The inventive salt of Example 1 was employed and evaluated as a charge agent in two different concentrations in toners and developers.

Toner samples were formulated from: 30 g toner binder comprising a crosslinked vinyl-addition polymer of styrene, butyl acrylate, and divinylbenzene (weight ratio: 77/23/1.35); 1.8 g of a carbon black pigment; and 0.3 and 0.9 g of the inventive salt. The formulations were melt-blended on a two-roll mill at 130° C., allowed to cool to room temperature, and ground down to form toner particles. Developers were prepared by mixing the toner particles (at a weight concentration of 13% toner) with carrier particles comprising strontium ferrite cores coated with poly(vinylidene fluoride). Toner charges were then measured in microcoulombs per gram of toner ($\mu c/g$). Previous experience has shown that a toner with well-dispersed charge agent will show increased charge as charge agent concentration is increased, but a toner with poorly dispersed charge agent will show decreased charge as charge agent concentration is increased. Results are presented in Table IV.

TABLE IV

| Inventive Charge Agent Concentration (g) in Toner | Toner Charge ($\mu c/g$) |
| --- | --- |
| 0.3 | 13.1 |
| 0.9 | 18.3 |

The data in Table IV indicate that the charging properties of toners and developers containing inventive charge agent were good, and that the charge agents were well dispersed in the toner particles (since the toner charge increased with increased charge agent concentration).

Similar results are achieved when the charge agent comprises benzylidmethyldodecylammonium 3,4-dimethoxycarbonylbenzenesulfonate.

The invention has been described in detail with particular reference to certain preferred embodiments thereof, but it should be appreciated that variations and modifications can be effected within the spirit and scope of the invention.

What is claimed is:

1. A quaternary ammonium salt having the structure

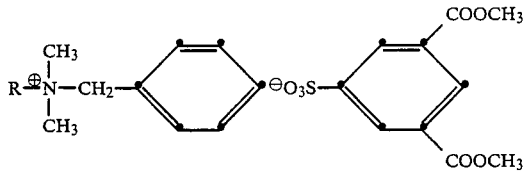

wherein R is alkyl having 12 to 18 carbon atoms.

2. The salt of claim 1, wherein R is $CH_3(CH_2)_{17}$.